US008389574B2

(12) United States Patent
Cavazza et al.

(10) Patent No.: US 8,389,574 B2
(45) Date of Patent: Mar. 5, 2013

(54) METHOD USEFUL FOR THE PREVENTION OF TYPE 2 DIABETES AND ITS COMPLICATIONS IN PRE-DIABETIC PATIENTS WITH INSULIN RESISTANCE

(75) Inventors: Claudio Cavazza, Rome (IT); Paolo Carminati, Milan (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 463 days.

(21) Appl. No.: 12/532,379

(22) PCT Filed: Mar. 21, 2008

(86) PCT No.: PCT/EP2008/053437
§ 371 (c)(1),
(2), (4) Date: Oct. 8, 2009

(87) PCT Pub. No.: WO2008/113862
PCT Pub. Date: Sep. 25, 2008

(65) Prior Publication Data
US 2010/0048691 A1 Feb. 25, 2010

(30) Foreign Application Priority Data
Mar. 21, 2007 (EP) .................................. 07104624

(51) Int. Cl.
*A61K 31/205* (2006.01)
*A61K 31/44* (2006.01)
*A61K 31/425* (2006.01)
*A61K 31/195* (2006.01)

(52) U.S. Cl. ........ 514/556; 514/356; 514/369; 514/561; 514/866

(58) Field of Classification Search .................. 514/556, 514/561, 369, 866, 356
See application file for complete search history.

(56) References Cited

U.S. PATENT DOCUMENTS

| 3,485,847 | A | * | 12/1969 | Friedrich et al. | 546/321 |
| 5,430,065 | A | * | 7/1995 | Cavazza | 514/556 |
| 5,925,656 | A | * | 7/1999 | Kallam et al. | 514/369 |
| 6,281,234 | B1 | * | 8/2001 | Kees | 514/365 |

FOREIGN PATENT DOCUMENTS

| WO | 98/01128 | 1/1998 |
| WO | 99/01126 | 1/1999 |
| WO | 00/74675 | 12/2000 |

OTHER PUBLICATIONS

McMackin et al., "Effect of Combined Treatment With α-Lipoic Acid and Acetyl-L-Carnitine on Vascular Function and Blood Pressure in Patients with Coronary Artery Disease", The Journal of Clinical Hypertension, vol. 9, No. 4, pp. 249-255 (2007).*
Rossmanith et al., "Comparison of the effects of L-carnitine and acetyl-L-carnitine on adipocyte glucose metabolism in spontaneously obese rats" International Journal of Obesity, vol. 18, No. suppl. 2, Aug. 25, 1994, p. 64.
Abuissa et al. "Angiotensin-Converting Enyzme Inhibitors or Angiotensin Receptor Blockers for Prevention of Type 2 Diabetes" Journal of the American College of Cardiology, vol. 46, No. 5, Sep. 6, 2005, pp. 821-826.
Sahib et al. "Prediabetes and hypertension" Journal of the Indian Medical Association, vol. 105, No. 1. Jan. 2007, pp. 25-28.
Jermendy et al. "Can type 2 diabetes mellitus be considered preventable?" Diabetes Research and Clinical Practice, vol. 68, Jun. 2005, pp. S73-S81.
Haffner et al. "Risk Constellations in Patients with the Metabolic Syndrome: Epidemiology, Diagnosis and Treatment Patterns" American Journal of Medicine, vol. 119, No. 5, May 2006, pp. S3-S9.
Peterson et al. "Impaired glucose tolerance and impaired fasting glucose-a review of diagnosis, clinical implications and management" Diabetes and Vascular Disease Research, vol. 2, No. 1, 2005, pp. 9-15.
Curtis et al. "Preventing type 2 diabetes mellitus" Journal of American Board of Family Practice, vol. 18, No. 1, 2005, pp. 37-43.
Scheen et al., "Renin-angiotensin system inhibition prevents type 2 diabetes mellitus" Diabetes and Metabolism, vol. 30, No. 6, Dec. 1, 2004, pp. 487-496.
Schernthaner, G. "Progress in the prevention of type 2 diabetes" Wiener Klinische Wochenschrift, vol. 115, No. 21-22, Nov. 28, 2003, pp. 745-757.
Miersch et al. "Antioxidant and antiplatelet effects of rosuvastatin in a hamster model of prediabetes" Free Radical Biology and Medicine, vol. 42, No. 2., Dec. 22, 2006, pp. 270-279.
Costa et al. "Effects of atorvastatin on glucose homeostasis, postprandial triglyceride response and C-reactive protein in subjects with impaired fasting glucose" Diabetic Medicine, vol. 20, No. 9, 2003, pp. 743-745.
Keech et al. "Secondary prevention of cardiovascular events with long-term pravastatin in patients with diabetes of impaired fasting glucose: Results from the LIPID trial" Diabetes Care, vol. 26, No. 10, Oct. 1, 2003, pp. 2713-2721.
Baron, A. "Impaired glucose tolerance as a disease" The American Journal of Cardiology, vol. 88, No. 6A, Sep. 20, 2001, pp. 16H-19H.

* cited by examiner

*Primary Examiner* — Kevin E Weddington
(74) *Attorney, Agent, or Firm* — Lucas & Mercanti, LLP

(57) ABSTRACT

The present invention relates to the use of acetyl L-carnitine in combination with an anti hypertensive drug, and a statin, for the preparation of a medicament for the prevention or delay of onset of type 2 diabetes and its complications, in pre-diabetic patients with insulin resistance.

16 Claims, No Drawings

METHOD USEFUL FOR THE PREVENTION OF TYPE 2 DIABETES AND ITS COMPLICATIONS IN PRE-DIABETIC PATIENTS WITH INSULIN RESISTANCE

CROSS-REFERENCE TO RELATED APPLICATIONS

This application is a 371 of PCT/EP2008/053437 filed on Mar. 21, 2008, which claims the benefit of European Patent Application No. 07104524.7 filed on Mar. 21, 2007, the contents of each of which are incorporated herein by reference.

FIELD OF THE INVENTION

The present invention relates to the use of acetyl L-carnitine in combination with an antihypertensive drug, and optionally or a statin, for the prevention or delay of onset of type 2 diabetes and its clinical complications in pre-diabetic subjects.

BACKGROUND OF THE INVENTION

Insulin resistance is a silent condition that increases the chances of developing type 2 diabetes. In insulin resistance condition the muscle, fat, and liver cells do not use insulin properly. The pancreas tries to keep up with the demand for insulin by producing more. Excess weight also contributes to insulin resistance because too much fat interferes with muscles' ability to use insulin. Lack of exercise further reduces muscles' ability to use insulin.

According to the American Diabetes Association, pre-diabetes can be defined as the state that occurs when a person's blood glucose levels are higher than normal but not high enough for a diagnosis of diabetes. About 11 percent of people with pre-diabetes in the Diabetes Prevention Program standard or control group developed type 2 diabetes each year during the average 3 years of follow-up. Other studies show that many people with pre-diabetes develop type 2 diabetes in 10 years.

Pre-diabetes was previously called Impaired Glucose Tolerance IGT and it has also been referred to as borderline or chemical diabetes. Insulin resistance and obesity linked to pre-diabetes can be an increased risk factor for hypertension, or high blood pressure which is one of the most important risk factors for cardiovascular disease, which can lead to a heart attack or stroke. If left untreated, hypertension can also lead to a wide variety of other life-threatening conditions, such as kidney damage and congestive heart failure.

People with pre-diabetes are, therefore, at higher risk of cardiovascular disease. People with pre-diabetes have a 1.5-fold risk of cardiovascular disease compared to people with normal blood glucose, whereas people with diabetes have a 2- to 4-fold increased risk of cardiovascular disease. Always according to the American Diabetes Association people with pre-diabetes can delay or prevent the onset of type 2 diabetes. This can be done through lifestyle changes.

An estimated 20 million people have pre-diabetes in the U.S. and this number is growing rapidly. 50 percent of the people who have pre-diabetes are likely to develop Type 2 diabetes.

Early diagnosis is important. In the early years of pre-diabetes or diabetes, the beta cells are progressively damaged by high blood sugars. Usually by the time diabetes is diagnosed, half of the beta cells are non-functional. This cannot be reversed so that the beta cells can go back to insulin production. However, when an early diagnosis of pre-diabetes is made, almost 100 percent of beta cells are functional. If lifestyle changes are made and some diabetes medications are used right away, many beta cells will stay healthy and make blood sugar control easier.

Diabetes or pre-diabetes can be detected and differentially diagnosed with one of the following tests:

Fasting Glucose Test, which measures blood glucose after not eating overnight. This test is most reliable when done in the morning. Fasting glucose levels of 100 to 125 mg/dL are above normal but not high enough to be called diabetes. This condition is called pre-diabetes or impaired fasting glucose (IFG), and it suggests that patient has probably had insulin resistance for some time. IFG is considered a pre-diabetic state, meaning that the patient is are more likely to develop diabetes but does not yet have it. Levels equal to or higher than 126 mg/dL are normally associated with diabetes.

Glucose Tolerance Test, which measures blood glucose after an overnight fast and 2 hours after patient drinks a sweet liquid provided by the doctor or laboratory. If patient blood glucose falls between 140 and 199 mg/dL, 2 hours after drinking the liquid, patient glucose tolerance is above normal but not high enough for diabetes. This condition, also a form of pre-diabetes, is called impaired glucose tolerance (IGT) and, like IFG, it points toward a history of insulin resistance and a risk for developing diabetes.

Levels equal to or higher than 200 mg/dL are normally associated with diabetes.

If conventional tests show that patient has IFG or IGT, the doctor may suggest changes in diet and exercise to reduce the risk of developing diabetes.

Insulin resistance is elusive, perhaps more easily identified than measurable. The WHO classification of the metabolic syndrome includes insulin resistance, but only when measured by hyperinsulinaemic euglycaemic clamp (Insulin Sensitivity Evaluation test). Using this test only people in the lowest quartile are defined as having insulin resistance. The clamp requires bilateral cannulation, arterialisation of blood flow to the vein and 2 hours of measures. The mean rate of glucose infusion during the last 30 minutes of the clamp is considered the insulin sensitivity index (ISI). Diabetes is a widespread disease present throughout the world and is associated with major clinical complications including microvascular complications such as diabetic retinopathy, diabetic neuropathy and diabetic nephropathy, and macrovascular complications such as atherosclerosis, peripheral vasculopathies, obesity, hypertension myocardial infarction, stroke, polycystic ovary syndrome and syndrome X (*J. Am. Osteopath. Assoc.*, 2000 October; 100(10):621-34; *Jama*, 2002 November, 27; 288(20):2579-88).

Said complications constitute a serious threat to the life and well-being of the individual.

Attempts to prevent the onset of type 2 diabetes have already been done. Researchers sponsored by the National Institute of Diabetes and Digestive and Kidney Diseases conducted the Diabetes Prevention Program (DPP) to find the most effective ways to prevent or delay the onset of type 2 diabetes. Volunteers were recruited from groups known to be at particularly high risk for IGT and type 2 diabetes. The study was designed to compare the effectiveness of lifestyle changes (weight loss through exercise and diet) with drug therapy (metformin). A control group received a placebo and information on diet and exercise. Participants assigned to the intensive lifestyle intervention reduced their risk of getting type 2 diabetes by 58 percent over 3 years.

Participants treated with metformin reduced their risk by 31 percent.

Drugs used for many years, such as the biguanides and sulphonylurea, are available on the market for the treatment of type 2 diabetes. Many of these, such as, for example, metformin, present gastrointestinal disorders, danger of acidosis in conditions of renal, cardiac, hepatic, pulmonary insufficiency, etc., as side effects. The sulphonylureas have episodes of hypoglycaemia as their possible side effects. Drugs recently introduced onto the market are the thiazolidonides, whose side effects such as liver toxicity, increased LDL cholesterol, weight gain and oedema have given cause for concern.

In WO 99/01126 is described a combination of statin and alkanoyl L-carnitines useful for treating diseases due to an altered lipid metabolism.

In WO00/74675 is described the use of carnitines for reducing the toxicity due to the administration of statins.

In Clin. Ter. 1992 January; 140(1 Pt 2):17-22 is described the hypotriglyceridemic action of L-carnitine in combination with simvastatin, in patient with renal failure.

In Atherosclerosis 188, 2006, 455-461 is described the efficacy of L-carnitine in combination with simvastatin in lowering Lipoprotein(a), in patient with type 2 diabetes.

In Minerva Medica, Vol. 80, N° 3 is described the use of L-carnitine for the treatment of hypertension in patient with type 2 diabetes. WO 98/01128 discloses the use of the acetyl L-carnitine, isovaleryl L-carnitine, propionyl L-carnitine to increase the levels of IGF-1. Diabetes is also included in the long list of curable pathologies reported in WO 98/01128.

WO 98/41113 describes a therapeutic nutritive composition for patients with diabetes mellitus consisting of gamma linoleic acid, acetyl L-carnitine, mineral salts and vitamins.

U.S. Pat. No. 4,362,719 describes the use of the L-carnitine and the acyl L-carnitine in treating the juvenile onset diabetes mellitus.

U.S. Pat. No. 5,430,065 describes the use of the L-carnitine and the acyl L-carnitine in the long-term treatment of those patients with non insulin-dependent diabetes.

In Journal of Cellular Physiology 203; 2005; 439-446 is reported that the addition of acetyl L-carnitine to the culture medium dramatically affected the ability of myocytes to respond to insulin treatment.

In these documents it is never mentioned the use of acetyl L-carnitine in combination with anti hypertensive drug for the prevention or delay of onset of type 2 diabetes and its clinical complications in pre-diabetic subjects.

Ever increasing attention is being devoted to the so-called risk factors recognised as underlying these diseases, and there is still a perceived need for a medicine capable of acting on the various sources of this pathological picture, without, at the same time, being associated with severe side effects, which, as in the case of certain antidiabetic drugs, may even make it necessary to discontinue the therapy.

DESCRIPTION OF THE INVENTION

It has now surprisingly been found that a certain combination of substances, known for their specific pharmacological actions, is particularly indicated for the prevention or delay of onset of type 2 diabetes in pre-diabetic subjects with insulin resistance.

According to the present invention insulin resistance was evaluated using the hyperinsulinaemic euglycaemic clamp test mentioned above. Using this test only people in the lowest quartile were defined as having insulin resistance. The mean rate of glucose infusion during the last 30 minutes of the clamp was considered to be the insulin sensitivity index (ISI).

The mean value of ISI was evaluated and patients with ISI below the median value (pre diabetic patients with more severe insulin resistance) were considered. The hyperinsulinaemic euglycaemic clamp test will be better described in the following.

According to the present invention pre diabetic patients are patients having glucose levels above normal but not high enough to be treated with antidiabetic drugs (fasting morning blood glucose between 100 to 125 mg/dl).

The combination of the invention has shown to be able to increase the sensitivity to insulin (particularly in patients with baseline ISI below the median value) and prevent or decrease hypertension in subjects likely to develop diabetes presenting three or more of the following factors: overweight or obesity; a family history of diabetes; women who have had gestational diabetes; steroid induced hyperglycemia; hypertension or an abnormal lipid profile.

The combination according to the invention comprises acetyl L-carnitine or a pharmaceutically acceptable salt thereof in combination with an antihypertensive drug, and optionally or a statin.

What is meant by pharmaceutically acceptable salt of acetyl L-carnitine is any salt of the latter with an acid that does not give rise to toxic or side effects.

These acids are well known to pharmacologists and to experts in pharmacy. Non-limiting examples of such salts are: chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethanesulphonate, methanesulphonate, choline tartrate, trichloroacetate, and trifluoroacetate.

What is meant by pharmaceutically acceptable salt of acetyl L-carnitine is also a salt approved by the FDA and listed in the publication *Int. J. of Pharm.* 33 (1986), 201-217, which is incorporated herein by way of a reference.

The combination according to the present invention is useful for decreasing insulin resistance and blood pressure particularly in pre-diabetic patients with insulin resistance already in treatment with anti hypertensive drugs; it is evident that decreasing insulin resistance and blood pressure is useful for the prevention or delay of onset of type 2 diabetes and its complications.

It is therefore one object of the present invention acetyl L-carnitine in combination with an antihypertensive drug, and optionally or a statin, for the prevention or delay of onset of type 2 diabetes and its clinical complications in pre-diabetic subjects.

It is a further object of the present invention acetyl L-carnitine in combination with an antihypertensive drug, and optionally or a statin, for the prevention or delay of onset of type 2 diabetes and its clinical complications in pre-diabetic subjects with insulin resistance.

It is a further object of the present invention acetyl L-carnitine in combination with an antihypertensive drug, and optionally or a statin, for the prevention or delay of onset of type 2 diabetes and its clinical complications in pre-diabetic subjects with a severe insulin resistance.

The clinical complications of diabetes, according to the present invention include: microvascular complications such as diabetic retinopathy, diabetic neuropathy and diabetic nephropathy; macrovascular complications such as atherosclerosis, peripheral vasculopathies; obesity; hypertension; myocardial infarction; stroke; polycystic ovary syndrome; and syndrome X.

It is a further object of the present invention acetyl L-carnitine, and optionally a statin, for the prevention or delay of onset of type 2 diabetes and its clinical complications, in pre-diabetic subjects with insulin resistance "already in treatment with an anti hypertensive drug".

"Already in treatment with anti hypertensive drugs" according to the present invention means that the treatment with an anti hypertensive drug was initiated before the treatment with acetyl L-carnitine and maintained during the treatment with acetyl L-carnitine.

It is a further object of the present invention acetyl L-carnitine, and optionally a statin, for the treatment of hypertension in pre-diabetic subjects already in treatment with an anti hypertensive drug.

It is a further object of the present invention acetyl L-carnitine, and optionally a statin, for the reduction of systolic blood pressure in pre-diabetic subjects already in treatment with an anti hypertensive drug.

It is a further object of the present invention acetyl L-carnitine, and optionally a statin, for the reduction of pulse blood pressure, in pre-diabetic subjects already in treatment with an anti hypertensive drug.

It is a further object of the present invention the use of acetyl L-carnitine, or a pharmaceutically acceptable salt thereof, in combination with an antihypertensive drug selected from the group consisting of: Alpha$_1$-Adrenergic Antagonists such as prazosin; Beta-Adrenergic Antagonists such as propranolol, nadolol, timolol, metoprolol, pindolol; ouabain antagonists such as rostafuroxin; Combined Alpha/Beta-Adrenergic Antagonists such as labetalol; Adrenergic Neuron Blocking Agents such as guanethidine, reserpine; CNS-Acting Antihypertensives such as clonidine, methyldopa and guanabenz; Angiotensin Converting Enzyme (ACE) Inhibitors such as spirapril, enalapril, ramipril, perindopril, indolapril, lysinopril, quinapril, pentopril, cilazapril, captopril, zofenopril, pivalopril and fosinopril; Angiotensin-II Receptor Antagonists such as losartan; Calcium Channel Blockers such as nicardipine, nimodipine, verapamil, diltiazem, nifedipine; Diuretics such as hydrochlorothiazide, chlorthalidone, furosemide, triamterene. Vasodilators such as hydralazine, minoxidil, nitroprusside, diazoxide, hydralazine, minoxidil, verapamil; and optionally or a statin selected from the group consisting of simvastatin, lovastatin, fluvastatin, pravastatin, atorvastatin, cerivastatin, rovastatin and rosuvastatin, the one preferred is simvastatin; for preparing a medicament for the prevention or delay of onset of type 2 diabetes and its clinical complications, in pre-diabetic subjects with insulin resistance.

It is a further object of the present invention the use of acetyl L-carnitine in combination with an antihypertensive drug, and optionally or a statin, for preparing a medicament for the treatment of hypertension in pre-diabetic subjects with insulin resistance.

It is a further object of the present invention the use of acetyl L-carnitine in combination with an antihypertensive drug, and optionally or a statin, for preparing a medicament for the reduction of systolic blood pressure in pre-diabetic subjects with insulin resistance.

It is a further object of the present invention the use of acetyl L-carnitine in combination with an antihypertensive drug, and optionally or a statin, for preparing a medicament for the reduction of pulse blood pressure, in pre-diabetic subjects with insulin resistance.

It is a further object of the present invention the use of acetyl L-carnitine, and optionally a statin, for preparing a medicament for the prevention or delay of onset of type 2 diabetes and its clinical complications, in pre-diabetic subjects with insulin resistance already in treatment with an anti hypertensive drug.

It is a further object of the present invention the use of acetyl L-carnitine, and optionally a statin, for preparing a medicament for the treatment of hypertension in pre-diabetic subjects already in treatment with an anti hypertensive drug.

It is a further object of the present invention the use of acetyl L-carnitine, and optionally a statin, for preparing a medicament for the reduction of systolic blood pressure in pre-diabetic subjects already in treatment with an anti hypertensive drug.

It is a further object of the present invention the use of acetyl L-carnitine, and optionally a statin, for preparing a medicament for the reduction of pulse blood pressure, in pre-diabetic subjects already in treatment with an anti hypertensive drug.

The combination according to the invention can also comprise other useful elements, without this substantially impairing the activity.

The combination according to the present invention can also be formulated as a food supplement, which constitutes a further object of the invention.

The medicine according to the invention can be used to prevent, or delay of onset, the individual disease states or to prevent a complex pathological picture that includes one or more of the therapeutic aspects seen above. For example, a medicine with a combined action for the reduction of hypertension, the prevention or delay of onset of type 2 diabetes and with an antilipaemic and protective action on the cardiovascular system, particularly in patients with pre-diabetes, insulin resistance and obesity.

DETAILED DESCRIPTION OF THE INVENTION

The combination according to the present invention comprises as active ingredients which are known in the medical sector and already used in clinical practice. Therefore, they are very easy to procure, inasmuch as they are products which have been on the market for some time and are of a grade suitable for human or animal administration.

The statins are a known class of drugs used for lowering cholesterol levels. Statins are available on the market or can be prepared according to known methods described in the literature. Acetyl L-carnitine is a known compound, the preparation process for which is described in U.S. Pat. No. 4,254,053.

The antihypertensive drugs are well known and widely used in the medical field.

The dosages and ratios of the individual components can be determined by the expert in the sector with normal preclinical and clinical trials, or with the usual considerations regarding the formulation of a dietetic product.

The amounts of the individual compounds advised for the preparation of a pharmaceutical composition for human use are the following.

Simvastatin: from 5 mg to 80 mg/day, preferably 15 to 40 mg/day; most preferably 20 mg/day.

Acetyl L-carnitine: from 0.5 to 5 g/day, preferably 1.5 to 3 g/day; most preferably 2 g/day.

The daily dose of the antihypertensive will depend, according to the judgement of the primary care physician, on the subject's weight, age, general condition of the patient and the type of antihypertensive drug used.

The pharmaceutical composition can have a unitary form, in which the active ingredients are present in a single pharmaceutical form (tablet, sachet, capsule, vial) or the active ingredients can be administered in a coordinated sequential manner. In the latter case, the pharmaceutical composition can be formulated, supplying the components in separate containers, accompanied by instructions for their sequential administration.

The compositions covered by the present invention are entirely conventional and are obtained with methods that are common practice in the pharmaceutical industry. According to the administration route opted for, the compositions will be in solid or liquid form, suitable for oral, parenteral or intravenous administration. The compositions according to the present invention contain, along with the active ingredient, at least one pharmaceutically acceptable vehicle or excipient. Particularly useful may be formulation adjuvants such as, for example, solubilising agents, dispersing agents, suspension agents and emulsifying agents. A general reference work is *Remington's Pharmaceutical Sciences Handbook*, latest edition.

The following example further illustrates the invention.

Example 1

Effects of Acetyl L-Carnitine for the Prevention or Treatment of Insulin Resistance, Blood Pressure and Metabolic Syndrome, in Pre Diabetic Patients Inclusion Criteria Forty subjects with fasting morning blood glucose $\leq 125$ mg/dl and at least three of the following criteria were considered eligible: First-degree relatives with type II diabetes, age 40 to 65 years, systolic or diastolic blood pressure $\geq 140$ or $\geq 90$ mmHg, respectively, body mass index (BM1) $\geq 25$ for men and $\geq 24$ for women, serum triglycerides $\geq 200$ mg/dl.

Exclusion Criteria

Those with serum creatinine $\geq 1.5$ mg/dl and urinary protein excretion rate $\geq 0.5$ g/24 h were excluded. Additional exclusion criteria were: concomitant treatment with steroids, anti-inflammatory and immunosuppressive agents, and any drug that may directly affect insulin sensitivity and/or insulin secretion including glitazones and oral antidiabetic agents, previous treatment with acetyl L-carnitine 6 months before the beginning of the study or concomitant treatment with metformin, inability to fully understand the purpose/risks of the study and to provide a written informed consent.

Study Design

Sequential off-on-off longitudinal study with a Run-In period, a 6-month Treatment Period and a 2-month Recovery Period.

Baseline Evaluation Included the Following Parameters:

Clinical:

Systolic/diastolic blood pressure; Heart rate; Body weight (SW); Body mass index (BMI);

Total body water (TBW) [(Calculated by the Hume and Weyers' formula:

TBW in males=(0.2968×weight in kg)+(0.1948×height in cm)−14.0129;

TBW in females=(0.1838×weight in kg)+(0.3446×height in cm)−35; 2701];

Fat-free mass (FFM) (Calculated: FFM=TBW/0.73);

Fat mass (FM) (Calculated: FM=BW−FFM).

Metabolic:

Fasting morning blood glucose; oral glucose tolerance test; HbAlc, insulin, leptin, adiponectin level; Lipid profile: total, LDL and HDL cholesterol, triglycerides, apolipoprotein A and B; Inflammatory marker: Erythrocyte sedimentation rate and C-reactive protein; Renal, Hepatic and Hematologic parameters: Serum creatinine; urea, sodium, potassium, uric acid, and creatin kinasis levels, haemoglobin concentration. Instrumental: Electrocardiogram.

For patients satisfying the inclusion/exclusion criteria the insulin sensitivity index (ISI) evaluated by an euglycemic hyperinsulinemic clamp (Calculated by the Hume and Weyers' formula; Diabetologia Volume 33, Number 4; April, 1990; 228-236) and then entered a six month treatment period with acetyl L-carnitine 2 g/day per oral route and with antihypertensive drugs (diuretics, ACE inhibitors, angiotensin II receptor antagonists, dihydro and non-dihydro calcium channel blockers) and/or statins were introduced throughout the whole study period.

Clinical, metabolic, lipid, inflammatory, renal, hepatic and hematologic parameters were evaluated every month during the treatment period and 2 months.

Insulin Sensitivity Evaluation (Euglycemic Hyperinsulinemic Clamp)

The insulin sensitivity was evaluated by means of an euglycemic hyperinsulinemic clamp according to D E, Fronzo R A, Tobin J A, Andres B. Glucose clamp technique, a method for quantifying insulin secretion and resistance. *Am J Physiol.* 1979; 237:214-223. The tests were done in the morning alter an overnight fast. The patients while lying supine, were inserted 2 cannulas. One in an antecubital vein for infusion of insulin and glucose, and the other was inserted into a contralateral vein for blood sampling. Before the start of the clamp; a blood sample was taken to determine the plasma levels of glucose, insulin, creatinine, lipids and HbA1c. The insulin infusion started with a concentration of 4.0 mU/kg/min for the first 10 minutes, followed by a concentration of 2.0 mU/kg/min for the rest of the duration of the test. The insulin was accompanied with 48 ml of isotonic salt infusion at a velocity of 25.2 ml/h for the first 10 minutes, and after that at a velocity of 12.6 ml/h. With the purpose to prevent the adhesion of the insulin to the walls of the syringe, is added 2 ml of blood to the solution. From the moment the first glucose had been infused, insulin was infused for 120 minutes. Parallely 500 ml of 20% glucose solution was supplemented by 20 mEq of potassium to prevent hypokaliemia. The infusion of the glucose solution started when the glucose concentration had reached a value of approximately 95 mg/dl. The glucose level was monitored every 5 minutes by the mean of a minimum of 2 determinations. The rate of glucose infusion was adjusted till a steady state with blood glucose levels of 90±5 mg/dl had been reached. The mean rate of glucose infusion during the last 30 minutes of the clamp was considered the insulin sensitivity index (ISI) or M value.

Laboratory and Instrumental Parameters

Fasting morning blood glucose oral glucose tolerance test, total cholesterol, LDL and HDL cholesterol, triglycerides, apolipoprotein A and B; erythrocyte sedimentation rate, creatinine, urea; sodium, potassium, uric acid, creatin kinasis, and haemoglobin were evaluated centrally by means of a Backman Syncron Cx5 instrument and a coulter Maxm (Beckman Coulter) and glycosylated haemoglobin (HbAlc) was measured with the use of ion-exchange high performance liquid chromatography.

Statistical Analyses

All analyses were completed using SPSS 13.0 for Windows. Clinical characteristics of the subjects selected were described using medias, standard deviations and percentages for continuous and categorical variables respectively.

Repeated-measures analysis of variance (ANOVA) to examine the effect of treatment on insulin sensitivity index; systolic/diastolic/mean/pulse blood pressure and other clinical, metabolic, lipid, inflammatory, renal, hepatic and hematologic parameters were made.

The metabolic syndrome was evaluated on the basis of the World Health Organization classification at baseline and at the end of the treatment period.

Results

Study Subjects

A total of 40 subjects entered the study four subjects withdrew. Thus, 36 subjects entered and completed the treatment period. The clinical characteristics of the 36 patients completing the treatment period are presented in Table 1.

TABLE 1

Baseline Clinical Characteristic of the Study Subjects

| Characteristic | Measure of location and spread* (n = 36) |
|---|---|
| Age (years) | 44.17 ± 9.07 |
| Gender | |
| Male | 23 (64%) |
| Female | 13 (36%) |
| History of Hypertension | 17 (47%) |
| History of cigarette smoking | |
| Current | 9 (25%) |
| Former | 7 (19%) |
| Never | 20 (56%) |
| Family history of type 1 diabetes mellitus (first and/or second degree) | 8 (22%) |
| Family history of type 2 diabetes mellitus (first and/or second degree) | 36 (100%) |
| Family history of Hypertension | 32 (89%) |
| Family history of CHD | 19 (53%) |
| Family history of CKD | 11 (31%) |
| Family history of CBV | 12 (33%) |
| Family history of Neuropathy | 5 (14%) |
| Systolic blood pressure mmHg | 137.43 ± 14.48 |
| Diastolic blood pressure mmHg | 83.84 ± 10.15 |
| Body mass Index (kg/m) | 31.653 ± 3.93 |
| Fasting glucose mg % | 96.13 ± 14.51 |
| Total cholesterol mg/dl | 217.07 ± 33.15 |
| HDL cholesterol mg/dl | 50.89 ± 10.49 |
| LDL cholesterol mg/dl | 148.72 ± 27.40 |
| Triglycerides mg/dl | 143.00 ± 130.55 |

CHD: Coronary Heart Diesease, CKD: Chronic Kidney Disease;
CBV: Cerebrovascular Disease;
ACEI/ARB; angiotensin-converting enzyme inhibitor or angiotensin receptor blocker.
*Data are presented as mean ± SD or number (percentage).

As shown, the majority of subjects were young adults, men and with a high prevalence of risk factors for cardiovascular disease and diabetes.

Participants were on antihypertensive therapy (see Table 2) and/or on lipid lowering therapy with statins.

TABLE 2

Anti hypertensive concomitant therapy
ANTIHYPERTENSIVE DRUGS

Diuretic
ACEI
ARB (angiotensin receptor blockers)
B-blocker
Alfa adrenergic blocker Effect of Treatment Insulin Resistance and the Metabolic Syndrome Patients with baseline ISI (Insulin Sensitivity Index) below the median value of 7.89 mg/kg/min (18 patients) were considered (these patients were pre diabetic patients with more severe insulin resistance).

Treatment with acetyl L-carnitine was associated with a statistically significant increase in ISI (p=0.044) see Table 3.

Consistently, the frequency of patients with the metabolic syndrome was significantly lower (p=0.021) at the end of the treatment period compared to baseline see Table 4.

TABLE 3

Effect of Acetyl-carnitine treatment on Insulin Sensitivity Index (ISI)

| TREATMENT (18 patients) | ISI (mean ± SD) | P |
|---|---|---|
| BEFORE | 4.79 ± 1.4 | — |
| AFTER | 6.72 ± 3.12 | 0.044 |

TABLE 4

Effect of Acetyl L-carnitine on Metabolic Syndrome (WHO classification)

| | Treatment | | |
|---|---|---|---|
| Patients | Before n/(%) | After n/(%) | p* |
| With MS | 16 (44.4%) | 8 (22.2%) | 0.021 |
| Without MS | 20 (55.6%) | 28 (77.8%) | |

*McNemar Test. Binomial distribution used.

The results reported above shown that the after six months treatment with acetyl L-carnitine significantly improved insulin sensitivity in patients with more severe insulin resistance.

The effect on insulin sensitivity was associated with a significant reduction in the proportion of patients with the metabolic syndrome (WHO criteria) at the end of the treatment period compared to baseline.

Effect of Treatment on Arterial Blood Pressure

In the 36 patients completing the treatment period, there was a statistically significant (p=0.003) effect of active treatment on systolic BP (Table V). When data at each time point during the treatment period were separately compared with baseline data by means of pair-wise comparisons with Bonferroni adjustments for multiple comparisons, treatment was associated with a significant reduction in systolic blood pressure (p<0.05) starting from the third month of treatment up to the end of the treatment period. Consistently with systolic blood pressure, also pulse pressure significantly decreased (p=0.008) during the treatment period. The reduction was statistically significant (p<0.05) starting from the fifth month to the end of the treatment-period (Table V).

TABLE V

Effect of Acetyl L-carnitine treatment on Blood Pressure in 36 patients completing the treatment period.

| | Systolic B.P. (mean ± SD) | Pulse P. (mean ± SD) |
|---|---|---|
| Baseline | 137.43 ± 14.48 | 53.58 ± 8.81 |
| 1 week | 132.56 ± 12.75 | 47.96 ± 8.37 |

TABLE V-continued

Effect of Acetyl L-carnitine treatment on Blood Pressure in 36 patients completing the treatment period.

|  | Systolic B.P. (mean ± SD) | Pulse P. (mean ± SD) |
|---|---|---|
|  |  | $p < 0.05$ |
| 1 month | 132.67 ± 12.57 | 50.43 ± 9.13 |
| 2 month | 132.53 ± 13.28 | 50.52 ± 11.02 |
| 3 months | 131.24 ± 13.09 $p < 0.05$ | 50.50 ± 8.12 |
| 4 months | 131.50 ± 13.89 $p < 0.05$ | 49.83 ± 10.09 |
| 5 months | 129.33 ± 15.65 $p < 0.05$ | 47.06 ± 10.09 $p < 0.05$ |
| 6 months | 129.52 ± 11.09 $p < 0.05$ | 48.55 ± 6.43 $p < 0.05$ |

These data show that treatment with acetyl L-carnitine was associated with a statistically significant reduction in systolic blood pressure and pulse pressure. These results have clinically relevant significance in reducing cardiovascular diseases.

The treatment with acetyl L-carnitine did not caused any effect on the on other metabolic, lipidic, inflammatory, renal, hepatic and hematologic parameters.

Six months acetyl L-carnitine therapy significantly improved insulin sensitivity in the subgroup of patients with more severe insulin resistance at inclusion. The effect on insulin sensitivity was associated with a significant reduction in the proportion of patients with the metabolic syndrome (WHO criteria) at the end of the treatment period compared to baseline.

In addition, treatment with acetyl L-carnitine was associated with a significant and clinically relevant reduction in systolic blood pressure and pulse pressure.

No adverse event was observed throughout the whole study period.

The invention claimed is:

1. Method for preventing or delay clinical complications of type 2 diabetes, in pre-diabetic subjects with insulin resistance comprising administering to a patient in need thereof a suitable amount of a composition comprising acetyl L-carnitine, or a pharmaceutically acceptable salt thereof, in combination with an antihypertensive drug.

2. The method of claim 1 wherein the pharmaceutically acceptable salt of acetyl L-carnitine is selected from the group consisting of: chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethanesulphonate, methanesulphonate, choline tartrate, trichloroacetate, and trifluoroacetate.

3. The method of claim 1 wherein the diabetes complications are selected from the group consisting of: microvascular complications comprising diabetic retinopathy, diabetic neuropathy and diabetic nephropathy; macrovascular complications comprising atherosclerosis, peripheral vasculopathies; obesity; hypertension; myocardial infarction; stroke; polycystic ovary syndrome; and syndrome X.

4. The method of claim 1 wherein the antihypertensive drug is selected from the group consisting of: $Alpha_1$-Adrenergic Antagonists comprising prazosin; Beta-Adrenergic Antagonists comprising propranolol, nadolol, timolol, metoprolol, pindolol; ouabain antagonists comprising rostafuroxin; Combined Alpha/Beta-Adrenergic Antagonists comprising labetalol; Adrenergic Neuron Blocking Agents comprising guanethidine, reserpine; CNS-Acting Antihypertensives comprising clonidine, methyldopa and guanabenz; Angiotensin Converting Enzyme (ACE) Inhibitors comprising spirapril, enalapril, ramipril, perindopril, indalapril, lysinopril, quinapril, pentopril, cilazapril, captopril, zofenopril, pivalopril and fosinopril; Angiotensin-II Receptor Antagonists comprising losartan; Calcium Channel Blockers comprising nicardipine, nimodipine, verapamil, diltiazem, nifedipine; Diuretics comprising hydrochlorothiazide, chlorthalidone, furosemide, triamterene, and Vasodilators comprising hydralazine, nitroprusside, diazoxide, hydralazine, minoxidil, verapamil.

5. The method of claim 4, wherein the calcium channel blocker is diltiazem, nifedipine, verapamil, nicardipine or nimodipine.

6. The method of claim 1, wherein the composition is in solid or liquid form, suitable for oral or parenteral administration in the form of tablet, sachet, capsule or vial.

7. The method of claim 1, wherein the composition is in a single pharmaceutical form or in separate containers for sequential administration.

8. Method for preventing or delay the clinical complications of type 2 diabetes, in pre-diabetic subjects with insulin resistance already in treatment with an anti-hypertensive drug, comprising administering to a patient in need thereof a suitable amount of acetyl L-carnitine, or a pharmaceutically acceptable salt thereof.

9. Method for reducing systolic blood pressure in pre-diabetic subjects already in treatment with an anti-hypertensive drug, comprising administering to a patient in need thereof a suitable amount of acetyl L-carnitine.

10. Method for reducing pulse blood pressure, in pre-diabetic subjects already in treatment with an anti-hypertensive drug, comprising administering to a patient in need thereof a suitable amount of acetyl L-carnitine.

11. Method of claim 8, wherein the pharmaceutically acceptable salt of acetyl L-carnitine is selected from the group consisting of: chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethanesulphonate, methanesulphonate, choline tartrate, trichloroacetate, and trifluoroacetate.

12. Method of claim 8 wherein the diabetes complications are selected from the group consisting of: microvascular complications comprising diabetic retinopathy, diabetic neuropathy and diabetic nephropathy; macrovascular complications comprising atherosclerosis, peripheral vasculopathies; obesity; hypertension; myocardial infarction; stroke; polycystic ovary syndrome; and syndrome X.

13. Method of claim 8, wherein the antihypertensive drug is selected from the group consisting of: alpha1-adrenergic antagonists comprising prazosin; beta-adrenergic antagonists comprising propranolol, nadolol, timolol, metoprolol, pindolol; ouabain antagonists comprising rostafuroxin; combined alpha/beta-adrenergic Antagonists comprising labetalol; adrenergic neuron blocking agents comprising guanethidine, reserpine; CNS-acting antihypertensives comprising clonidine, methyldopa and guanabenz; angiotensin converting enzyme (ACE) inhibitors comprising spirapril, enalapril, ramipril, perindopril, indolapril, lysinopril, quinapril, pentopril, cilazapril, captopril, zofenopril, pivalopril and fosinopril; angiotensin-II receptor antagonists comprising losartan; calcium channel blockers comprising nicardipine, nimodipine, verapamil, diltiazem, nifedipine; diuretics comprising hydrochlorothiazide, chlorthalidone, furosemide, triamterene; vasodilators comprising hydralazine nitroprusside, diazoxide, hydralazine, minoxidil, verapamil.

14. Method of claim 13, wherein the calcium channel blocker is diltiazem, nifedipine, verapamil, nicardipine or nimodipine.

15. Method of claim 8, wherein the medicament is in solid or liquid form, suitable for oral or parenteral administration in the form of tablet, sachet, capsule or vial.

16. Method of claim 8, wherein the medicament is in a single pharmaceutical form or in separate containers for sequential administration.

* * * * *